US006956155B1

(12) United States Patent
Martinez-Force et al.

(10) Patent No.: US 6,956,155 B1
(45) Date of Patent: Oct. 18, 2005

(54) HIGH OLEIC HIGH STEARIC PLANTS SEEDS AND OILS

(75) Inventors: Enrique Martinez-Force, Sevilla (ES); Juan Munoz-Ruz, Cordoba (ES); Jose Maria Fernandez-Martinez, Cordoba (ES); Rafael Garces, Valencia de la Concepcion (ES)

(73) Assignee: Consejo Superior de Investigaciones Cientificas, Sevilla (ES)

( * ) Notice: Subject to any disclaimer, the term of this patent is extended or adjusted under 35 U.S.C. 154(b) by 133 days.

(21) Appl. No.: 10/009,066

(22) PCT Filed: Jun. 5, 2000

(86) PCT No.: PCT/EP00/05150

§ 371 (c)(1),
(2), (4) Date: May 16, 2002

(87) PCT Pub. No.: WO00/74470

PCT Pub. Date: Dec. 14, 2000

Related U.S. Application Data

(63) Continuation-in-part of application No. 09/326,501, filed on Jun. 4, 1999, now Pat. No. 6,388,113.
(60) Provisional application No. 60/180,455, filed on Feb. 4, 2000.

(30) Foreign Application Priority Data

Dec. 17, 1999 (EP) ................................. 99204384

(51) Int. Cl.⁷ ........................... A01H 5/00; C12N 15/82
(52) U.S. Cl. ...................... 800/322; 800/260; 800/281; 800/298
(58) Field of Search ............................... 800/298, 281, 800/260, 322

(56) References Cited

U.S. PATENT DOCUMENTS

| 4,627,192 | A | 12/1986 | Fick |
| 5,147,792 | A | 9/1992 | Perchorowicz et al. |
| 5,298,421 | A | 3/1994 | Davies et al. |
| 5,304,481 | A | 4/1994 | Davies et al. |
| 5,344,771 | A | 9/1994 | Davies et al. |
| 5,443,974 | A | 8/1995 | Hitz et al. |
| 5,558,871 | A | 9/1996 | Griat et al. |
| 5,795,969 | A | 8/1998 | Fehr et al. |
| 5,850,026 | A | 12/1998 | DeBonte et al. |
| 5,885,643 | A | 3/1999 | Kodali et al. |
| 6,365,802 | B2 * | 4/2002 | Kridl ........................ 800/312 |

FOREIGN PATENT DOCUMENTS

| DE | 3831516 A1 | 3/1990 |
| EP | 0 561 569 A2 | 9/1993 |
| WO | WO 89/03419 A1 | 4/1989 |
| WO | WO 91/16421 A1 | 10/1991 |
| WO | WO 92/11373 A1 | 7/1992 |
| WO | WO 92/20236 A1 | 11/1992 |
| WO | WO 93/18158 A1 | 9/1993 |
| WO | WO 95/20313 A1 | 8/1995 |
| WO | WO 96/06936 A1 | 3/1996 |
| WO | WO 97/12047 A1 | 4/1997 |

OTHER PUBLICATIONS

Battey et al, TIBTECH 7: 122-126, May 1989.*
Ruiz-Gutierrez, V., et al., "Composition of Human VLDL Triacylglycerols After Ingestion of Olive Oil and High Oleic Sunflower Oil," *Journal of Nutrition* 128(3): 570-576, 1998 (abstract only).
Alvarez-Ortega, R., et al., "Characterization of Polar and Nonpolar Seed Lipid Classes From Highly Saturated Fatty Acid Sunflower, Mutants," *Lipids* 32(8):833-837, 1997 (abstract only).
Wen-Hsiung, L., and Y.-C. Chi, "Interesterifaction of Vegetable Oils Using an Immobilized Sn-1, 3-Specific Lipase Adsorbed on Solid Carriers," *Journal of Chinese Agricultural Chemical Society* 35(4):355-364, 1997 (abstract only).
Marquez-Ruiz, G., et al., "Thermoxidative Stability of Triacylglycerols From Mutant Sunflower Seeds," *Journal of the American Oil Chemists' Society* 76(10):1169-1174, 1999 (abstract only).
Martinez-Force, E., and R. Garces, "New Oilseed Varieties With Modified Fatty Acid Composition in the Oil," *Trends in Agronomy* 2:13-21, 1999.
Osorio, J., et al., "Mutant Sunflowers With High Concentration of Saturated Fatty Acids in the Oil," *Crop Science* 35(3):739-742, 1995.
Garces, R., and M. Mancha, "One-Step Lipid Extraction and Fatty Acid Methyl Esters Preparation From Fresh Plant Tissues," *Analytical Biochemistry* 211:139-143, 1993.
Rock, C.O., et al., "Preparative Enzymatic Syntheses of Acyl-Acyl Carrier Protein," *Methods in Enzymology* 72: 397-403, 1981.
Facciotti, M.T., et. al., "Improved Stearate Phenotype in Transgenic Canola Expressing a Modified Acyl-Acyl Carrier Protein Thioesterase," *Nature Biotechnology* 17:593-597, 1999.
Alvarez-Ortega, R., et al., "Characterization of Polar and Nonpolar Seed Lipid Classes From Highly Saturated Fatty Acid Sunflower Mutants," *Lipids* 32(8):833-837, 1997.

(Continued)

*Primary Examiner*—Elizabeth F. McElwain
(74) *Attorney, Agent, or Firm*—Christensen O'Connor Johnson Kindness PLLC

(57) ABSTRACT

The invention relates to plant seeds that contain an oil having an oleic acid content of more than 40 wt % and a stearic acid content of more than 12 wt % based on the total fatty acid content of said oil, and wherein a maximum of 10 wt % of the fatty acid groups in the sn-2 position of the TAG molecules constituting the oil are saturated fatty acid groups. The invention also relates to plants that can be grown from the seeds, oil that can be extracted from the seeds, and to methods for obtaining the seeds, plants and oil.

13 Claims, 5 Drawing Sheets

OTHER PUBLICATIONS

Garces, R., et al., "Sunflower Mutants with Increased Levels of Palmitic and Stearic Acids in the Oil," *Proceedings of the 14th International Sunflower Conference,* Beijing-Shenyang, P.R. China, Jun. 12-20, 1996, pp. 612-615.

Alvarez-Ortega, R., et al., "Fatty Acid Composition of Different Tissues During High Stearic or High Palmitic Sunflower Mutants Germination," in J.P. Williams et al. (eds.), *Physiology, Biochemistry and Molecular Biology of Plant Lipids,* Kluwer Academic Publishers, Dordrecht, The Netherlands, 1997, pp. 322-324.

Cantisán, S., et. al., "Maturation Changes and Temperature Effect on Fatty Acid Composition in Developing High Saturated Sunflower (*Helianthus annuus*) Seeds, " Advances in Plant Lipids Research, *Proceedings of the 13th International Symposium on Plant Lipids,* Sevilla, Spain, Jul. 1998, pp. 125-130.

Martinez-Force, J.M., et. al., "Inheritance of High Stearic Acid Content in the Seed Oil of Sunflower," Advances in Plant Lipids Research, *Proceedings of the 13th International Symposium on Plant Lipids,* Sevilla, Spain, Jul. 1998, pp. 134-136.

Martinez-Force, E., et. al., "Fatty Acid Composition in Developing High Saturated Sunflower (*Helianthus annuus*) Seeds: Maturation Changes and Temperature," *Journal of Agricultural and Food Chemistry* 46(9):3577-3582, 1998.

Garces, R., et. al., "Sunflower Mutants with Altered Fatty Acid Composition in the Seed Oil," in J.-C. Kader et al. (eds.), *Plant Lipid Metabolism*, Kluwer Academic Publishers, Dordrecht, The Netherlands, 1995, pp. 512-514.

Cantisán, S., et. al., "Lipid Characterization in Vegetative Tissues of High Saturated Fatty Acid Sunflower Mutants," *Journal of Agricultural and Food Chemistry* 47(1):78-82, 1999.

Hawkins, D.J., and J.C. Kridl, "Characterization of Acyl-ACP Thioesterases of Mangosteen (Garcinia Mangostana) Seed and High Levels of Stearate Production in Transgenic Canola," *The Plant Journal* 13(6):743-752, 1998.

* cited by examiner

HIGH OLEIC HIGH STEARIC PLANTS SEEDS AND OILS

CROSS-REFERENCES TO RELATED APPLICATIONS

This application is the National Stage of International Application No. PCT/EP00/05150, filed Jun. 5, 2000, which claims the benefit of U.S. Provisional Application No. 60/180,455, filed Feb. 4, 2000, and which is a continuation-in-part of U.S. application Ser. No. 09/326,501, filed Jun. 4, 1999 (now U.S. Pat. No. 6,388,113).

FIELD OF THE INVENTION

The present invention relates to new seeds that contain an oil having a high oleic and high stearic content. The invention also relates to plants producing these seeds and to the oil that is contained in the seeds. In addition, the invention relates to methods for producing the seeds, plants and oil.

BACKGROUND OF THE INVENTION

The uses of oils are determined by their fatty acid composition. The principal component of oils are the triacylglycerol (TAG) molecules, which constitute normally more than 95% of the oil. Three fatty acids are bound to a molecule of glycerol to make the TAG. If these fatty acids are mainly saturated fatty acids ("saturates") the product is called fat and it is solid at room temperature. On the other hand if the fatty acids are mainly unsaturated then it is called oil and it is liquid at room temperature.

The oils obtained from seeds cultivated in temperate climate (sunflower, soybean, rapeseed, etc.) have mainly unsaturated fatty acids, like linoleic and oleic acids, so they are liquid and primarily used for cooking, salad dressing, etc. Fats are obtained from animals (margarine, lard, etc.), some tropical trees (cocoa, palm) or chemically modified (hydrogenation and transesterification) liquid vegetable oils. They have mainly saturated (palmitic or stearic acids) or chemically modified fatty acids (trans fatty acids) all with high melting point.

Table 1 shows as an example the fatty acid composition and other properties of some fats and oils. The fats are needed for most of the food industry to make margarine, shortening, bakery, confectionery, snacks, etc. The food industry uses the fat for these purposes because of their plastic properties (they do not melt, can be spread, or do not stick to the hand) and stability (they have a good resistance to oxidation at room or high temperatures).

The actual available fats are however not a good option because they have negative nutritional properties. The main problem is that they raise the bad form of serum cholesterol (low density lipoprotein, LDL). This is due to several facts, some related to the origin of the fat and others with the manipulation thereof. Animal fats have most of the saturated fatty acids in the position 2 of the TAG molecule. Most vegetable fats and oils, however, have only minor amounts of saturated fatty acids in this position and are therefore more healthy.

During digestion the TAG molecule is hydrolysed by enzymes called lipases (FIG. 1). The fatty acids in positions 1 and 3 are liberated as free fatty acids. If these fatty acids are saturated they form insoluble salts with calcium and magnesium, being mostly excreted. But fatty acids in position 2 form with the glycerol a molecule of monoacylglycerol, which has detergent properties and is easily absorbed into the body. The saturated fatty acids from animal fats are then absorbed, thus raising LDL.

In order to increase the percentage of saturated fatty acids, vegetable oils are hydrogenated and/or transesterified. The hydrogenation process produces trans fatty acids that probably are even worse than saturated fatty acids as illustrated by Willett, W. C. & Ascherio, A. (1994) Trans fatty acids: Are the effects only marginal? American Journal of Public Health 84:722–724. The transesterification process changes randomly the fatty acids within the three positions, converting a healthy vegetable oil with low saturated fatty acid in the 2 position in an oil that has near 30% of saturated fatty acids. So neither of the two chemical modifications leads to a healthy product.

However, not all fats are unhealthy. It has been demonstrated that cocoa butter, which has around 60% of saturated fatty acids, the rest being mainly oleic acid, does not raise serum cholesterol. This is due to two main reasons. One is that only 4% of the saturated fatty acids are in position 2 and the other is that the principal saturated fatty acid is stearic acid. Stearic acid does not have a negative effect on serum cholesterol. Probably the amount of 35% of oleic acid in the cocoa butter also adds to its healthy property.

It is important to note that except in cocoa butter, palmitic acid is the main saturated fatty acid of commodity fats. Palmitic is however not a very healthy fat.

Traditional breeding and mutagenesis has not been the only tool used to form seeds producing oil with different fatty acid profiles. Increases in stearic acid in oil bearing

TABLE 1

| Oil or fat | Fatty acid composition (%) | | | | | | Properties | |
|---|---|---|---|---|---|---|---|---|
| | Others[1] | Myristic | Palmitic | Stearic | Oleic | Linoleic | Trans | Saturated |
| Lard | 3 | 2 | 25 | 12 | 45 | 10 | 1 | 79 |
| Butter | 14 | 10 | 26 | 12 | 28 | 3 | 3 | 84 |
| Margarine | | | 10 | 7 | 46 | 34 | 23 | — |
| Palm oil | | 1 | 45 | 5 | 39 | 9 | | 18 |
| Olive oil | 1 | | 14 | 3 | 71 | 10 | | 2 |
| Cocoa butter | | | 26 | 35 | 35 | 3 | | 4 |
| Normal sunflower | | | 7 | 5 | 30 | 57 | | 1 |
| High oleic sunflower | | | 5 | 4 | 88 | 2 | | 1 |

[1]"others" are palmitoleic in the case of lard and olive oil and also fatty acids shorter than 12 carbons in butter
*depends on the level of hydrogenation plants have also been addressed by the introduction of transgenes into the germplasm, to alter the fatty acid biosynthesis pathway of the vegetable oil. The fatty acid biosynthesis in vegetable oil, but more particularly sunflower oil, includes the biosynthesis of basically two saturates (palmitate, stearate) and two unsaturates (oleate and linoleate). In oilseeds, the stearoyl-ACP desaturase is the enzyme which introduces the first double bond on stearoyl-ACP to form oleoyl-ACP. Thus, this is an enzyme that assists in the determination of the unsaturation in the C18 length fatty acids.

In U.S. Pat. No. 5,443,974 the inhibition of canola enzyme stearoyl-ACP desaturase was described. The stearate levels were increased but the levels of palmitate were basically unaffected. Inhibition of the plant enzyme stearoyl-ACP desaturase in canola was also reported by Knutzon et al., Proc. Natl. Acad. Sci. USA 89:2624–28 (1992). These results showed an increase in the level of stearate produced in the canola seed. The research also showed that inhibition by antisense in seeds of canola and soybean, respectively, showed increased stearate. When a plasmid containing a gene encoding for stearoyl-ACP desaturase was placed in canola, this inhibition resulted in an increase in stearic acid but unfortunately a reduction in the oleate. However, in the soybean this inhibition of stearate resulted in a less dramatic reduction of the oleate. This slower decrease in oleate however may have been a function of the small initial levels of oleate in the soybean. The fatty acid pathway in most oilseed plants appears to be resistant to maintaining both oleic and stearic at elevated levels.

PCT/US97/01419 describes increased levels of both stearic acid and palmitic acid in sunflowers through the inhibition of the plant enzyme stearoyl-ACP desaturase. As indicated above, palmitic oil is not, however, viewed as being a very healthy oil.

PCT/US96/09486 discloses that sunflower oil levels of both palmitic and oleic acids could be increased, the seeds having increased levels of palmitic acid of 21–23% and of oleic acid of 61%. The sunflower oil is liquid at room temperature. But the increased palmitic fatty acid level is alleged to allow the oil to be used in shortening and in margarine with relatively low level of hydrogenation, which leads to a relatively low level of trans-fatty acids in the resulting product. However, the commercial value may be questioned because of the high level of palmitic acid.

There thus remains a need for a sunflower oil which is both healthy and useful for industrial purposes. Furthermore, it is desirable to have a sunflower oil that has a balance of good saturates and good unsaturates, i.e. that is high in unsaturates but has sufficient saturates to be used for margarines or hardstock without high levels of hydrogenation, thus leading to no trans-fatty acids in the resulting product. Basically, there remains a need for a sunflower plant that can produce seed containing oil which is high in oleic acid and in stearic acid with reduced linoleic levels.

SUMMARY OF THE INVENTION

It is therefore the object of the present invention to provide a vegetable oil with high stearic acid (as saturated fatty acid) and high oleic acid (as unsaturated fatty acid) contents that will reduce the above described problems with fat. In this oil the stearic acid should preferably be in positions 1 and 3 of TAG.

The present invention is based on the following considerations. The seed fatty acid biosynthesis occurs inside the plastid (FIG. 2). A series of cycling reactions catalysed by the enzymatic complex FAS I produces the palmitoyl-ACP that has 16 carbons. A second enzymatic complex called FAS II elongates the palmitoyl-ACP to stearoyl-ACP (18 carbons), that is further modified by the stearate desaturase to produce oleoyl-ACP. These are the three main fatty acids synthesised by the plastid, being cleaved off the ACP by the action of the enzyme thioesterase and then exported out of the plastid. Later in the cytoplasm, the oleic acid may be desaturated to linoleic and linolenic acids.

The TAG (storage oil) is produced in the cytoplasm using the pool of fatty acids in the cytoplasm. This fatty acid pool consists of the fatty acids exported from the plastid and the linoleic acid made in the cytoplasm by desaturation. Thus, the fatty acid composition of TAG is determined by the fatty acids exported out of the plastid plus the linoleic acid produced in the cytoplasm.

It was then contemplated that a new plant that is rich in stearic and oleic acids could be selected if a reduced stearate desaturase activity (leading to a decrease in the amount of oleoyl-ACP formed and therefore in an increase in the stearoyl-ACP) was combined with a good thioesterase activity on stearoyl-ACP (which leads to the stearic acid being transported out of the plastid into the cytoplasm). This plant will produce an accumulation of stearoyl-ACP inside the plastid, and the good activity of the thioesterase over stearoyl-ACP should export it very well out of the plastid, having there a high stearic acid content available for TAG biosynthesis.

Out of the plastid, in the cytoplasm the high oleic character is necessary to keep the linoleic acid content low. In high oleic lines, the conversion pathway does not work properly, so there is no conversion of oleic acid to linoleic acid.

The present invention is thus based on the finding that by selection of one parent line that has a high stearic (HS) acid content on the one hand and a second parent line having a high oleic and high thioesterase (HOHT) activity over stearoyl-ACP on the other hand, crosses can be made that result in seeds having a combination of the high stearic and high oleic properties (HSHO). In addition, it was surprisingly found that in said oil a maximum of 10 wt % of the fatty acid groups in the sn-2 position of the TAG molecules are saturated fatty acid groups.

Therefore, the present invention relates to plant seeds that contain an oil comprising an oleic acid content of more than 40 wt % and a stearic acid content of more than 12 wt % based on the total fatty acid content of said oil, and wherein a maximum of 10 wt % of the fatty acid groups in the sn-2 position of the TAG molecules constituting the oil are saturated fatty acid groups. Preferably, the saturated fatty acid groups are stearic acid groups. It is preferred that the oil has in the sn-2 position of the TAG molecules a maximum of 8%, more preferably a maximum of 5 wt % of saturated fatty acid groups, in particular stearic acid groups.

Regarding the other fatty acids, it is preferred that the oleic acid content is from 55 to 75 wt %, the stearic acid content is from 15 to 50 wt %, in particular 20 to 40 wt %, and the linoleic acid content is less than 20 wt %. Preferably the total level of saturated fatty acids is at least 20 wt %.

Selection of the parents can be achieved as follows.

Lines with high stearic acid content are lines having a stearic acid content of more than 12%, preferably more than 20%. One example of such a high stearic (HS) parent line, which was selected after mutagenesis and has a stearic acid content of 26 wt %, is available as "CAS-3" (ATCC deposit no. 75968, deposited on Dec. 14, 1994). Another example is "CAS-4", having a stearic acid content of 16.1 wt % (ATCC deposit no. 75969, deposited on Dec. 14, 1994). By analysing the fatty acid composition of oil derived from the seeds of other candidate lines, the skilled person will be able to select other suitable parent lines.

It was found that some of the usual high oleic varieties could not be used for the purpose of the invention because they were found to have very low thioesterase activity over the stearoyl-ACP. To overcome this, by measuring the thioesterase activity, lines with good activity over stearoyl-ACP can be selected from the available high oleic lines collections.

In short, one would first analyse the fatty acid composition of the oil of several promising lines. A suitable HOHT parent line would have more than 7–8% stearic acid and either less than 5% linoleic acid or more than 75% oleic acid. Subsequently, the selected lines must be grown and self pollinated. The total thioesterase activity is measured in seeds 15 days after flowering (15DAF) on both oleoyl-ACP and stearoyl-ACP. In suitable lines, the activity over stearoyl-ACP should be more than 10% of the activity over oleoyl-ACP. The ratio between both activities determines whether a line is suitable as a parent line or not.

In Table 2 the fatty acid composition and thioesterase activity of two high oleic sunflower lines are illustrated.

TABLE 2

Stearic acid content and thioesterase Vmax over the stearoyl-ACP of 15 days after flowering seeds from two high oleic sunflower lines.

| Sunflower line | Stearic acid (%) | Thioesterase activity Vmax |
|---|---|---|
| HOHT | 17.8 | 2.03 |
| HOLT | 8.0 | 0.82 |

The HOHT line is a high oleic line with thioesterase over stearoyl-ACP activity (HOHT) of more than twice the thioesterase Vmax over stearoyl-ACP than an usual high oleic line (HOLT). The relative activity of the enzymes over the stearoyl-ACP standardised with respect to the one over oleoyl-ACP is illustrated in FIG. 3. This line has as a consequence more stearic acid at 15 days after flowering (Table 2) and also in the oil obtained from the mature seed (Table 3).

TABLE 3

Fatty acid composition (%) of seeds from two high oleic sunflower lines.

| | Fatty acid composition (%) | | | | | |
|---|---|---|---|---|---|---|
| Sunflower line | palmitic | stearic | oleic | linoleic | araquic | behenic |
| HOHT | 4.3 | 9.7 | 78.5 | 3.9 | 1.0 | 2.6 |
| HOLT | 3.8 | 4.9 | 84.3 | 4.8 | 0.5 | 1.7 |

This HOHT parent line was deposited on Sep. 7, 1999 with the American Type Culture Collection (10801 University Boulevard, Manassas, Va. 20110-2209) and was assigned the number PTA-628.

Lines of both types (HOHT and HOLT) have been crossed with the high stearic CAS-3 line. In FIG. 4 (for HOHT) and 5 (for HOLT), the F2 segregation for both traits (high stearic acid content and high oleic acid content) are shown. The seeds with higher content in stearic and oleic acids are within a circle. From the figures it follows that the HOHT line with high thioesterase activity over stearoyl-ACP has high oleic high stearic seeds and the line without high thioesterase activity has no seeds of this type. Table 4 shows the fatty acid composition of these lines.

TABLE 4

Fatty acid composition of selected high oleic and stearic lines, with high and low thioesterase activity over stearoyl-ACP, after crossing with HS line CAS-3

| | Fatty acid composition (%) | | | | | |
|---|---|---|---|---|---|---|
| Sunflower line | palmitic | stearic | oleic | linoleic | araquic | behenic |
| HOHTxCAS-3 | 5.2 | 24.6 | 59.2 | 6.8 | 1.8 | 2.4 |
| HOLTxCAS-3 | 4.3 | 17.4 | 72.1 | 4.0 | 1.3 | 2.8 |

The selected F2 lines are selfed for 5 to 6 generations in isolated conditions to avoid contamination. The resultant generations are selected, based on high oleic and stearic acid content. Thioesterase activity can be analysed to assist in the selection process. Likewise, marker assisted breeding can be employed to track any or all of the three traits to make the selection process quicker. Various markers such as SSR microsatellite, ASO, RFLP and likewise can be employed. The use of markers is not necessary, as standard tests are known for determining oleic, stearic, and thioesterase activity. However, once identified markers make trait tracking easier and earlier in the plant's life.

The true breeding plants produce an oil having a similar fatty acid composition to the F2 seeds selected with a low content of saturated fatty acid in the 2 position of the TAG molecule (Table 5).

TABLE 5

Fatty acid composition of oil, TAG and sn-positions of true breeding HSHO plants selected. n.d. = not detected.

| | Fatty acid composition (mol %) | | | | | |
|---|---|---|---|---|---|---|
| | Palmitic | Stearic | Oleic | Linoleic | Araquic | Behenic |
| Total oil | 5.5 | 24.9 | 57.8 | 8.2 | 1.7 | 1.8 |
| TAG | 5.6 | 26.1 | 57.6 | 7.4 | 1.6 | 1.7 |
| sn-2 position | 1.7 | 1.9 | 87.4 | 9.0 | n.d. | n.d. |
| sn-1 and 3 position | 7.2 | 33.1 | 46.8 | 7.3 | 2.7 | 2.9 |

The invention also relates to plants which form seeds which contain the above described oil of the invention and to the oil per se as well as to products derived from the seeds, such as meal and crushed seeds. The plants, seeds, oil, meal and crushed seeds of the invention are for example sunflower plants, seeds, oil, meal and crushed seeds.

The plants and seeds of the invention are obtainable by a method comprising:
   a) providing seeds which contain an oil having its a stearic acid content of at least 3.2 wt % based on the total fatty acid content of the oil;
   b) providing seeds which contain an oil having an oleic acid content of at least 40 wt % based on the total fatty acid content of the oil, and which have a thioesterase activity over stearoyl-ACP that is at least 10% of the thioesterase activity over oleoyl-ACP;
   c) crossing plants grown from the seeds provided in step (a) and (b);
   d) harvesting the F1 seed progeny.

Preferably, the method further comprises the steps of:

e) planting the F1 progeny seeds to grow plants;

f) self-pollinating the plants thus grown to produce F2 seed;

g) testing the seed for the presence of a stearic acid content in the oil of at least 12 wt % and an oleic acid content of at least 40 wt % and a thioesterase activity over stearoyl-ACP that is at least 10% of the thioesterase activity over oleoyl-ACP;

h) planting seeds having the desired levels of stearic acid content, oleic acid content and thioesterase activity to grow plants;

i) self-pollinating the plants thus grown to produce F3 seed; and j) optionally repeating steps g), h) and i) until the desired levels of stearic acid content, oleic acid content and thioesterase activity are fixed.

Preferably, the stearic acid content is at least 15 wt %, preferably at least 20 wt %.

The present invention also covers the method of obtaining an oil, in particular a sunflower oil, having an oleic acid content of more than 40 wt % and a stearic acid content of more than 12 wt % based on the total fatty acid content of the oil by extracting oil from the seeds. The method preferably includes an extraction process which does not involve a substantial modification of the (sunflower) oil.

Additionally, in the process of extraction of the oil from the seeds there is preferably no substantial chemical or physical modification nor enzymatic rearrangement taking place and preferably no substantial hardening of the oil.

The present invention also includes food products comprising oil obtainable from seeds, in particular sunflower seeds, having an oleic acid content of more than 40 wt % and a stearic acid content of more than 12 wt % based on the total fatty acid content of the oil. Food products that are particularly useful for this type of oil include spreads, margarines, shortenings, sauces, ice-cream, soups, bakery products, confectionery products, and the like. In these food products the level of (sunflower) oil is preferably from 3 to 100 wt % relative to the total oil weight in the product. When used to form a spread according to the present invention the (sunflower) oil is preferably used as a hardstock at levels of 5 to 20 wt %.

The sunflower seeds of the present invention are also suitable per se for human and animal consumption.

The present invention also encompasses cosmetic products comprising an oil, in particular a sunflower oil, the oil having an oleic acid content of more than 40 wt % and a stearic acid content of more than 12 wt % based on the total fatty acid content of the oil. These cosmetic products can preferably contain levels of (sunflower) oil from 3 to 100 wt %. Some examples of these cosmetic products would include creams, lotions, lipsticks, soap bars and skin or hair oils.

The present invention also includes a process for selecting *Helianthus annuus* plants, capable of producing seeds having the desired oil. The steps of the method are a) selecting a number of *Helianthus annuus* plants, collecting therefrom the seeds, the oil of which has a stearic acid content of at least 12 wt % and preferably 18 wt % based on the total fatty acid content; (b) selecting a number of *Helianthus annuus* plants, collecting therefrom the seeds, which express an oleic acid content of at least 40 wt % based on the oil present in the seed and a thioesterase activity over stearoyl-ACP that is at least 10% of the thioesterase activity over oleoyl-ACP; (c) crossing the plants grown from the seeds of (a) and (b); and, harvesting the F1 seed progeny.

Additional steps include the steps of: (d) planting of the seeds or embryo rescue of the embryos of the F1 progeny obtained to form F2 segregating seeds; (e) selecting from the F2 seeds which developed plants, those plants which produce seeds having an oleic acid content of more than 40 wt % and a stearic acid content of more than 12 wt % based on the total fatty acid content of the oil, optionally selfing the selected plant to form true breeding inbreds.

The present invention also includes the process for producing F1 hybrid seed. The steps of the method are a) planting seed of two inbreds having high oleic acid content of at least 40 wt % and thioesterase activity over stearoyl-ACP that is at least 10% of the thioesterase activity over oleoyl-ACP, one of which may be male sterile, b) crossing the two inbreds, and c) harvesting the F1 seed capable of producing F2 seed with an at least 40 wt % oleic acid content and an at least 12 wt % stearic acid content.

The present invention encompasses a vegetable oil with a new and unique fatty acid composition produced in easy to grow crops. The preferred crop is sunflower. This plant was used for making this invention. However, the invention is more broadly applicable and selection of suitable parents to produce the derived vegetable oil could likewise modify other crops. These crops would include at least *Brassicas*, peanuts, palms and other oil producing plants. When mutation is used for making one or both of the parents, the crop should be susceptible to mutagenically induced oil changes. Rape seed meets all these requirements as does sunflower, these crops are presently some of the most useful crops for production of this new and unique fatty acid composition in the oil of their seeds.

BRIEF DESCRIPTION OF THE DRAWINGS

In this application reference is made to the following figures.

DETAILED DESCRIPTION OF THE INVENTION

Definitions

Figure 1:
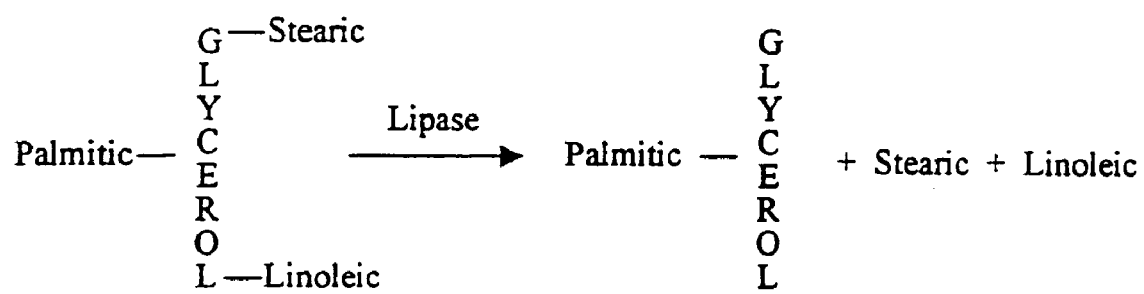
FIG. 1: hydrolysis of triacylglycerols by lipase.
Figure 2:
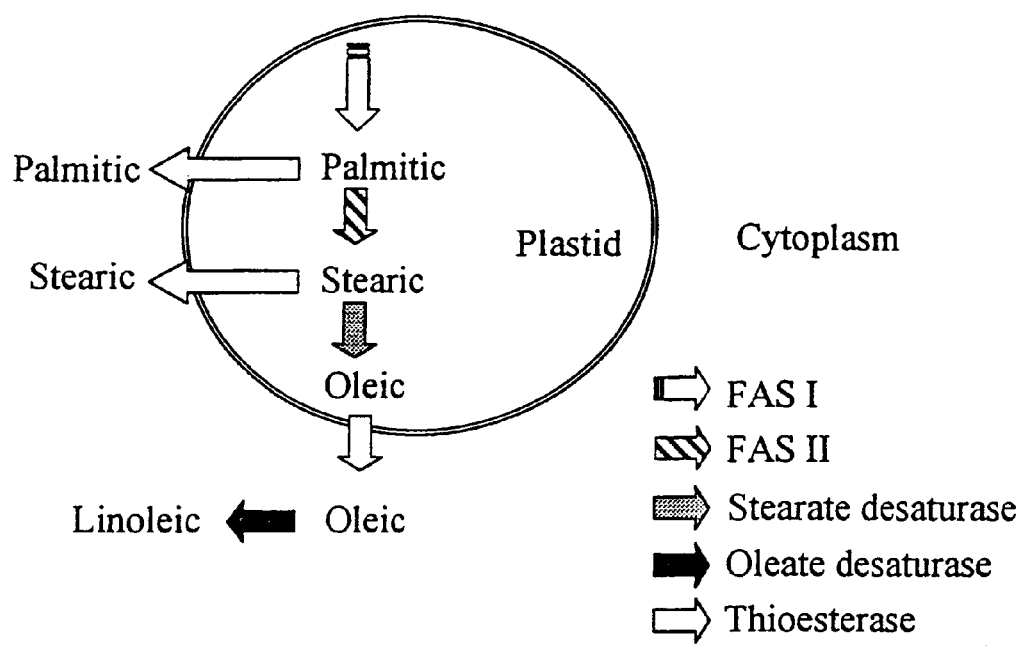
FIG. 2: plastid showing the fatty acid biosynthesis in oilseeds.
Figure 3:
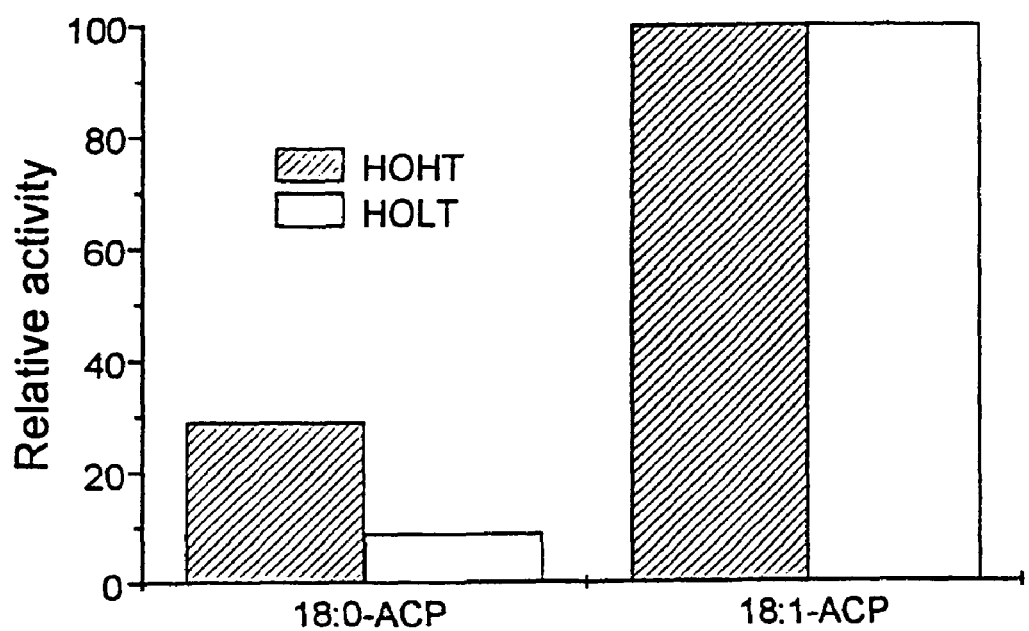
FIG. 3: elevated thioesterase activity shown as the relative activity of the thioesterase over stearoyl-ACP and oleoyl-ACP of HOHT and HOLT.
Figure 4:
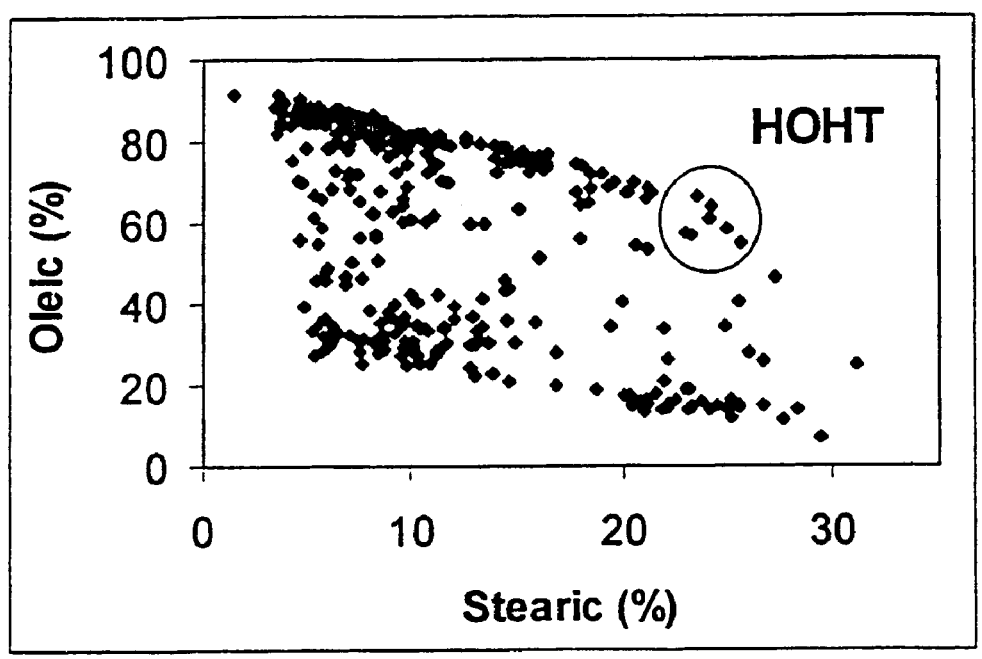
FIG. 4: the F2 segregation for stearic and oleic acids of the cross between high oleic with high thioesterase activity over stearoyl-ACP line (HOHT) and a high stearic acid line (CAS-3)
Figure 5:
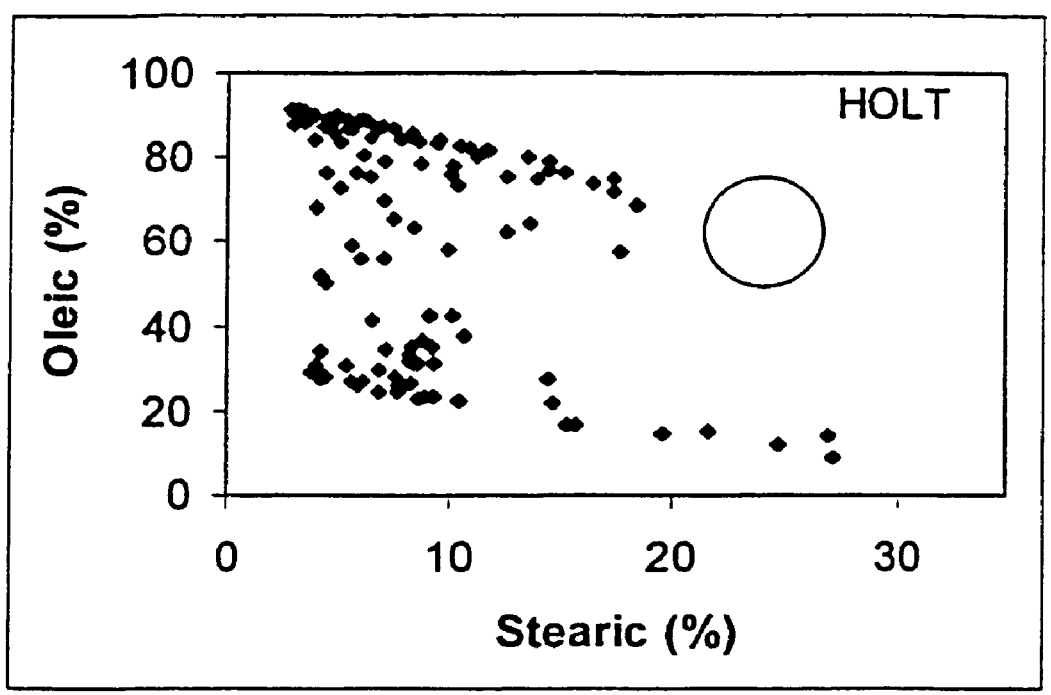
FIG. 5: the F2 segregation for stearic and oleic acids of the cross between high oleic with low thioesterase activity over stearoyl-ACP line (HOLT) and a high stearic acid line (CAS-3).

"SUNFLOWER" shall mean *Helianthus annuus*.

"PLANT" shall include the complete plant and all plant and cell parts including pollen, kernel, oil, embryo, stalk, head, roots, cells, meristems, ovule, anthers, microspores, embryos, DNA, RNA, petals, seeds, and the like and protoplasts, callus or suspensions of any of the above.

"15DAF" shall mean 15 days after flowering.

"TOTAL FATTY ACID CONTENT" of the sunflower oil refers to the sum of C16:0, 18:0, 18:1, 18:2, 20:0, 22:0 and the traces of other like fatty acids as determined simultaneously in the oil from the seed.

"HOLT" shall mean having high to medium-high (40%–90%) oleic acid levels in the oil when compared to normal, wildtype sunflower seed (oleic acid levels of 17%–20%) wherein there are "LOW LEVELS OF THIOESTERASE ACTIVITY". A "HOLT LINE" is a line, in particular a sunflower line, having the HOLT trait.

"HOHT" shall mean having high to medium-high (40%–90%) oleic acid levels in the oil when compared to normal, wildtype sunflower seed (oleic acid levels of 17%–20%) wherein there are "HIGH LEVELS OF THIOESTERASE ACTIVITY". A "HOHT LINE" is a line, in particular a sunflower line, that has the HOHT trait.

"HIGH LEVELS OF THIOESTERASE ACTIVITY" shall mean levels (at 15DAF) of thioesterase activity over stearoyl-ACP which are at least 10% of the thioesterase activity over oleoyl-ACP. Consequently, "LOW LEVELS OF THIOESTERASE ACTIVITY" shall mean levels which are below the "HIGH LEVELS OF THIOESTERASE ACTIVITY".

"HS" shall mean having stearic acid levels in the oil of at least 12 wt % and preferably at least 15 wt % or more preferably at least 18 wt % or even at least 20 wt % based on the total fatty acid content. "HIGH STEARIC LINE" or "HS LINE" shall mean a line, in particular a sunflower line, having the HS trait.

"HOHS" shall mean having levels of above 40% oleic acid and at least 12 wt % stearic acid in the oil and preferably having levels of at least 15% wt, more preferably at least 18 wt % or even at least 20 wt % stearic acid in the oil. A "HOHS LINE" shall mean a line having the HOHS trait.

EXAMPLES

Introduction

Preparation of HS Parent

In order to obtain the HS parent a method can be used for preparing sunflower seeds having an increased stearic acid and oleic acid content as compared to wild type seeds. This method includes the step of treating parent seeds with a mutagenic agent during a period of time and in a concentration sufficient to induce one or more mutations in the genetic trait involved in stearic acid or oleic acid biosynthesis. This results in an increased production of stearic acid and/or an increased level of oleic acid. These mutagenic agents include agents such as sodium azide or an alkylating agent, like ethyl methane sulfonate, of course any other mutagenic agent having the same or similar effects may also be used. The treated seeds will contain inheritable genetic changes. These mutated seeds are then germinated and progeny plants are developed therefrom. To increase the traits in the lines the progeny can be crossed or selfed. The progeny seeds are collected and analysed.

Sodium azide and ethyl methane sulfonate were used as mutagenic agents in Example 1. Several sunflower lines with a stearic acid content between 12 and 45% have been obtained. In all these cases the original sunflower parent line for the production of the high stearic acid lines used was RDF-1–532 (Sunflower Collection of Instituto de Agricultura Sostenible, CSIC, Cordoba, Spain) that has from 4 to 7% stearic acid content in the seed oil.

Selecting the HOHT Parent

In principle it is sufficient to screen oleic lines for a HOHT phenotype and use this line for either transformation or for crossing to a high stearic line to develop a HOHS line. A suitable line is at least the HOHT parent line that was deposited on Sep. 7, 1999 with the American Type Culture Collection (10801 University Boulevard, Manassas, Va. 20110-2209) and was assigned the number PTA-628.

Making the HOHS Line

Seeds having the HOHT trait or the stearic trait can then be crossed to each other to form the HOHS line. Optionally there can be additional cycles of germination, culturing, and selfing to fix the homozygosity of the traits in the lines and crossing and collection of seeds.

Materials and Methods

Plants Growth Conditions

Sunflower (*Helianthus annuus* L.) seeds from high oleic lines with altered seed fatty acid content was used to test for the thioesterase activities over stearoyl-ACP. Plants were cultivated in growth chambers at 25/150° C. (day/night) temperature, 16 hours photoperiod and photon flux density of 300 micromol $m^{-2}s^{-1}$. Seeds for analysis were harvested at 15 days after flowering and kept at –20° C.

Radioactive Reagents and Preparation of Acyl-ACPs $1-^{14}C$-Oleic with specific radioactivity of 2.1 GBq/mmol and (9, 10(n)-$^3$H) stearic acid with specific radioactivity of 1.9 GBq/mmol were obtained from American Radiolabeled Chemicals Inc. (St. Louis, Mo., USA). To prepare the fatty acid sodium salt, an appropriate volume of fatty acid solution was transferred to a glass tube, the solvent was removed under a stream of nitrogen, and the residue was dissolved in 10% Triton X-100, 0.6 mM NaOH. This solution was heated at 55° C. for 1 hour to ensure homogeneity.

Acyl-ACPs were prepared using a modification of the enzymatic synthesis procedure of Rock C.O. et al. (1981) Methods Enzymology 72:397–403. Assays contained 0.1 M Tris-HCl (pH 8.0), 0.4 M LiCl, 5 mM ATP, 10 mM $MgCl_2$, 2 mM DTT, 130 microM fatty acid sodium salt, 0.27 mM ACP-SH and 1.8 mU of acyl-ACP synthetase (the last two components were purchased from Sigma-Aldrich Quimica S.A. Madrid, Spain) in a final volume of 110 microliter. Reactions were incubated at 37° C. for 3 hours. After this time the pH was acidified to 6.0 by adding 1 microliter of 3.6 M HCl and the mixture was cleaned of free fatty acids using a modification of the method described by Mancha M. et al. ((1975) Anal. Biochem. 68:600–608), which method consists of adding an equal volume of isopropanol and washing three times with hexane saturated in water/isopropanol (1:1; v/v).

Preparation of Crude Extracts for Enzyme Assays and Protein Determination

Frozen seeds were peeled and ground in extract buffer containing 20 mM Tris-HCl (pH 8.5), 2 mM DTT and 5% (v/v) glycerol (Dörmann P. et al. (1994) Biochim. Biophys. Acta 1212:134–136) at 1 g of tissues/10 ml of buffer. Protein concentrations were measured using a Protein Assay Kit (Bio-Rad) according to the manufacturer's recommendations, with BSA as standard.

Enzyme Assays

Acyl-ACP thioesterase activity was assayed in a final volume of 170 microliter using 130 microliter of crude extract. Control assays had crude extract omitted. Reactions mixtures contained 20 mM Tris-HCl (pH 8.5), 5% glycerol and 2 mM dithiothreitol (DTT) and different concentrations of substrates (stearoyl-ACP and oleoyl-ACP). Incubations were carried out for 20 min at 25° C. Reactions were stopped by the addition of 170 microliter of 1 M acetic acid in isopropanol containing 1 mM of oleic acid. Mixtures were then washed three times with hexane saturated in water/isopropanol (1:1, v/v).

Acyl-ACP thioesterase activity was determined by counting the radioactivity of the aqueous phase, which contained the non-hydrolysed substrates. Then, 3 ml of solvent scintillant (purchased from National Diagnostics, Hessle, England) was added and the radioactivity was measured using a scintillation counter (Rackbeta II; LKB, Sweden). Data from acyl-ACP thioesterase assays were fitted to the Michaelis-Menten equation by non-linear least-squares regression analysis using Microcal Origin 4.1, and correlated to $P<0.05$, as determined by paired Student's test. Vmax and Km were derived from these curves.

Example 1

Preparation of a HS Line

1. Mutation with EMS

Seeds were mutagenised with a solution of 70 mM of ethyl methane sulfonate (EMS) in water. The treatment was performed at room temperature during 2 hours while shaking (60 rpm). After mutagenesis the EMS solution was discarded and seeds were washed during 16 hours under tap water.

Treated seeds were germinated in the field and plants were self-pollinated. The seeds collected from these plants were used to select new sunflower lines with modifications in the fatty acid composition. By using the method of Garcés, R. and Mancha, M. ((1993) Anal. Biochem. 211, 139–143) the seed fatty acid composition was determined by gas liquid chromatography, after converting the fatty acids into their corresponding methyl esters.

A first plant with 9 to 17% stearic acid content in the oil was selected. The progeny was cultivated for five generations wherein the stearic acid content increased and the new genetic trait became stably fixed in the genetic material of the seed. This line is called CAS-3. The minimum and the maximum stearic acid content of the line were 19 and 35% respectively. The stearic acid content of oil extracted from seeds from this cell line may thus lie between 19 and 35%.

2. Mutation with Sodium Azide

Sunflower seeds were mutagenised with sodium azide, at a concentration of 2 mM in water. The treatment was performed at room temperature during two hours while shaking (60 rpm). Then the mutagenesis solution was discarded and seeds were washed during 16 hours with tap water.

Seeds were planted in the field and plants were self-pollinated. Seeds from these plants were collected, and the fatty acid composition was determined by gas liquid chromatography, after converting the fatty acids into their corresponding methyl esters using the method described in Example 1.

Seeds from a plant having around 10% stearic acid in the oil were selected and cultivated for five generations. During this procedure the stearic acid content was increased and the new genetic trait fixed. This line is called CAS-4. A selected sample of this line was analysed resulting in a stearic acid content of 16.1%. The minimum and the maximum values were 12 and 19%, respectively.

TABLE 6

| Line | Percentage fatty acids | | | |
|---|---|---|---|---|
| | Palmitic | Stearic | Oleic | Linoleic |
| CAS-3 | 5.1 | 26.0 | 13.8 | 55.1 |
| CAS-4 | 5.5 | 16.1 | 24.3 | 54.1 |

CAS-3 and CAS-4 are on deposit with the American Type Culture Collection, having ATCC numbers 75968 and 75969, respectively.

Example 2

Production of a HSHO Line

1. General

Sunflower plants were grown from the sunflower seeds of the HOHT line, seeds of which are on deposited at ATCC (PTA-628). Sunflower plants were also grown from the sunflower seeds of CAS-3. The lines were crossed. The plants were assisted by artificial pollination in order to ensure adequate seed production occurred. The F1 seed was produced on the HOHT line, or vice versa, and harvested. The F2 seeds with more than 20% stearate and more than 40% oleate were selected. Although this produces the oil of the present invention the level of production is limited.

Therefore fixed inbred lines evidencing seeds with these oil profiles are desirable. These homozygous fixed inbred HSHO lines can then be crossed to form hybrid seed, which will produce F2 seed evidencing the desired oil traits of the present invention.

Toward this end the F1 seeds were planted and produced plants were selfed in isolated conditions and F2 seed was produced. The F2 seed was tested for the three traits, high stearic, high oleic and high levels of thioesterase activity. The remaining portion of the seeds evidencing these traits was employed to grow plants to form F3 seed. The selfing and screening and selection process is repeated to develop the fixed homozygous HSHO line, having the following fatty acid profile, C:16 5.4, C, 18.0 24.8, C, 18.1 58.5, C, 18.2 7.2. Once the trait is fixed similar HSHO lines can cross to form hybrid seed having both traits.

According to the invention sunflower plants and seeds from which said oil can be extracted have been obtained by means of a biotechnological process. This high stearic acid content is an inheritable trait and is fairly independent from the growing conditions.

2. First Cross

A sunflower plant was grown from a sunflower seed of an HOHT line having a stearic acid content of 10.7 wt % and an oleic acid content of 74.6 wt %. A sunflower plant was also grown from a CAS-3 sunflower seed. The plants were crossed. The plants were assisted by artificially pollination in order to ensure adequate seed production occurred. The F1 seed was produced on the HOHT line, or vice versa, and harvested.

A F1 seed having a stearic acid content of 9.8 wt % and an oleic acid content of 80.7 wt %, was selected. This F1 seed was planted and produced a plant which was selfed in isolated conditions and F2 seeds were produced. These F2 seeds were tested for oleic and stearic acid contents. A seed containing 23.6 wt % of stearic acid and 65.5 wt % of oleic acid was selected.

This F2 seed was planted and produced a plant which was selfed in isolated conditions and at 15DAF several seeds were collected and analysed for stearoyl-ACP thioesterase activity. Plants with seeds rendering more than 10% stearoyl-ACP thioesterase referred to the oleoyl-ACP thioesterase activity of the same plant were selected.

Mature seeds from the plants selected in the previous step and having stearic acid content higher than 20 wt % and oleic acid content higher than 40 wt % were submitted to the selfing, screening and selection process repeatedly to develop the fixed homozygous high stearic high oleic line having the following fatty acid profile in the oil:
- palmitic 7.8 wt %;
- stearic 24 wt %;
- oleic 57.7 wt %;
- linoleic 5.9 wt %;
- araquic 1.9 wt %;
- behenic 2.7 wt %.

Once the trait is fixed, similar high stearic high oleic lines can cross to form hybrid seed having the above selected traits.

An analysis of the sn-2 position and sn-1,3 positions of the TAG molecules of this oil indicates the following distribution of fatty acids (in wt %):

sn-2:
- palmitic 3.3%;
- stearic 3.4%;
- oleic 88.8%;
- linoleic 4.5%;
- araquic 0%;
- behenic 0% sn-1,3:
- palmitic 9%;
- stearic 29.9%;
- oleic 51.1%;
- linoleic 4.7%;
- araquic 2.3%;
- behenic 3%

Thus, the total amount of saturated fatty acid groups in the sn-2 position of the TAG molecules of this oil is 6.7 wt %.

3. Second Cross

A sunflower plant was grown from a sunflower seed of an HOHT line having a stearic acid content of 8.4 wt % and an oleic acid content of 78.5 wt %. A sunflower plant was also grown from a CAS-3 sunflower seed. The plants were crossed. The plants were assisted by artificially pollination in order to ensure adequate seed production occurred. The F1 seed was produced on the HOHT line, or vice versa, and harvested. A F1 seed having a stearic acid content of 7.1 wt % and an oleic acid content of 84.6 wt %, was selected. This F1 seed was planted and produced a plant which was selfed in isolated conditions and F2 seeds were produced. These F2 seeds were tested for oleic and stearic acid contents. A seed containing 22.8 wt % of stearic acid and 64.8 wt % of oleic acid was selected.

This F2 seed was planted and produced a plant which was selfed in isolated conditions and at 15 DAF several seeds were collected and analysed for stearoyl-ACP thioesterase activity. Plants with seeds rendering more than 10% stearoyl-ACP thioesterase referred to the oleoyl-ACP thioesterase activity of the same plant were selected. Mature seeds from the plants selected in the previous step and having stearic acid content higher than 20 wt % and oleic acid content higher than 40 wt % were submitted to the selfing, screening and selection process repeatedly to develop the fixed homozygous high stearic high oleic line having the following fatty acid profile in the oil:
- palmitic 5.8 wt %;
- stearic 24, 7 wt %;
- oleic 57.6 wt %;
- linoleic 8.2 wt %;
- araquic 1.8 wt %;
- behenic 1.9 wt %.

Once the trait is fixed, similar high stearic high oleic lines can cross to form hybrid seed having the above selected traits.

An analysis of the sn-2 position and sn-1,3 positions of the TAG molecules of this oil indicates the following distribution of fatty acids (in wt %):

sn-2:
- palmitic 1.7%;
- stearic 1.9%;
- oleic 87.5%;
- linoleic 8.9%;
- araquic 0%;
- behenic 0% sn-1,3:
- palmitic 7.2%;
- stearic 33.2%;
- oleic 46.9%;
- linoleic 7.3%;
- araquic 2.6%;
- behenic 2.8%.

Thus, the total amount of saturated fatty acid groups in the sn-2 position of the TAG molecules of this oil is 3.6 wt %.

4. Third Cross

A sunflower plant was grown from a sunflower seed of an HOHT line having a stearic acid content of 9.9 wt % and an oleic acid content of 81.2 wt %. A sunflower plant was also grown from a CAS-3 sunflower seed. The plants were crossed. The plants were assisted by artificially pollination in order to ensure adequate seed production occurred. The F1 seed was produced on the HOHT line, or vice versa, and harvested.

A F1 seed having a stearic acid content of 8.9 wt % and an oleic acid content of 82.3 wt %, was selected. This F1 seed was planted and produced a plant which was selfed in isolated conditions and F2 seeds were produced. These F2 seeds were tested for oleic and stearic acid contents. A seed containing 23.9 wt % of stearic acid and 64.0 wt % of oleic acid was selected.

This F2 seed was planted and produced a plant which was selfed in isolated conditions and at 15 DAF several seeds were collected and analysed for stearoyl-ACP thioesterase activity. Plants with seeds rendering more than 10% stearoyl-ACP thioesterase referred to the oleoyl-ACP thioesterase activity of the same plant were selected. Mature seeds from the plants selected in the previous step and having stearic acid content higher than 20 wt % and oleic acid content higher than 40 wt % were submitted to the selfing, screening and selection process repeatedly to develop the fixed homozygous high stearic high oleic line having the following fatty acid profile in the oil:
- palmitic 5.4 wt %;
- stearic 24, 2 wt %;
- oleic 62.1 wt %;
- linoleic 4.7 wt %;
- araquic 1.6 wt %;
- behenic 2.0 wt %.

Once the trait is fixed, similar high stearic high oleic lines can cross to form hybrid seed having the above selected traits.

An analysis of the sn-2 position and sn-1,3 positions of the TAG molecules of this oil indicates the following distribution of fatty acids (in wt %):

sn-2:
  palmitic 1.8%;
  stearic 3.3%;
  oleic 89.6%;
  linoleic 5.3%;
  araquic 0%;
  behenic 0% sn-1,3:
  palmitic 9.5%;
  stearic 33.5%;
  oleic 48.2%;
  linoleic 4.3%;
  araquic 2.2%;
  behenic 2.3%

Thus, the total amount of saturated fatty acid groups in the sn-2 position of the TAG molecules of this oil is 5.1 wt %.

The present application pertains to genetic material, comprising plant seeds, which include the oil contained therein, meal and crushed seeds, as well as the process of growing the seeds and the plants that are the result from growing the seeds and plants producing the seeds.

What is claimed is:

1. Sunflower seeds that contain oil having an oleic acid content of more than 40 wt % and a stearic acid content of more than 12 wt % based on the total fatty acid content of said oil, wherein a maximum of 10 wt % of the fatty acid groups in the sn-2 position of the triacylglycerol molecules are saturated fatty acids, and wherein the oil has a linoleic acid content of less than 20 wt %.

2. Sunflower seeds according to claim 1, wherein the seeds contain an oil that has in the sn-2 position of the triacylglycerol molecules constituting the oil a maximum of 8 wt % of saturated fatty acid groups.

3. Sunflower seeds according to claim 2, wherein the seeds contain an oil that has in the sn-2 position of the triacylglycerol molecules constituting the oil a maximum of 5 wt % of saturated fatty acid groups.

4. Sunflower seeds according to claim 1, wherein the oleic acid content is from 55 to 75 wt %.

5. Sunflower seeds according to claim 1, wherein the stearic acid content is from 15 to 50 wt %.

6. Sunflower seeds according to claim 5, wherein the stearic acid content is from 20 to 40 wt %.

7. Sunflower seeds according to claim 1, wherein the oil has a total level of saturated fatty acids of at least 20 wt %.

8. Method for producing a sunflower plant which forms seeds as claimed in claim 1, which method comprises:
  a) providing sunflower seeds which contain oil having a stearic acid content of at least 12 wt %;
  b) providing sunflower seeds which contain an oil having an oleic acid content of at least 40 wt % and a thioesterase activity over stearoyl-ACP of at least 10% of the thioesterase activity over oleoyl-ACP;
  c) crossing sunflower plants grown from the sunflower seeds provided in step a) and b);
  d) harvesting the F1 seed progeny.

9. Method as claimed in claim 8, further comprising the steps of:
  e) planting the F1 progeny seeds to grow sunflower plants;
  f) self-pollinating the sunflower plants thus grown to produce F2 seed;
  g) testing the seed for the presence of a stearic acid content of at least 12 wt %, an oleic acid content of at least 40 wt % and a thioesterase activity over stearoyl-ACP of at least 10% of the thioesterase activity over oleoyl-ACP;
  h) planting sunflower seeds having a stearic acid content of at least 12 wt %, an oleic acid content of at least 40 wt %, and a thioesterase activity over stearoyl-ACP of at least 10% of the thioesterase activity over oleoyl-ACP to grow sunflower plants;
  i) self-pollinating the sunflower plants thus grown to produce F3 seed; and
  j) optionally repeating steps g), h) and i) until the stearic acid content of at least 12 wt %, the oleic acid content of at least 40 wt %, and the thioesterase activity over stearoyl-ACP of at least 10% of the thioesterase activity over oleoyl-ACP are fixed.

10. Method as claimed in claim 8, wherein the seeds which contain oil having a stearic acid content of at least 12 wt % are provided by:
  a) mutagenic treatment of sunflower seeds having a stearic acid content of less than 12%;
  b) producing sunflower plants therefrom which are pollinated to produce seeds;
  c) testing the seeds for the desired stearic acid content; and
  d) optionally repeating steps b) and c).

11. Sunflower plants obtained by the method of claim 8.
12. Sunflower plants obtained by the method of claim 9.
13. Sunflower plants obtained by the method of claim 10.

* * * * *